(12) United States Patent
Mahfouz (10) Patent No.: US 11,435,425 B2
(45) Date of Patent: Sep. 6, 2022

(54) IMU CALIBRATION

(71) Applicant: TechMah Medical, LLC, Knoxville, TN (US)

(72) Inventor: Mohamed R. Mahfouz, Knoxville, TN (US)

(73) Assignee: TECHMAH MEDICAL LLC, Knoxville, TN (US)

( * ) Notice: Subject to any disclaimer, the term of this patent is extended or adjusted under 35 U.S.C. 154(b) by 0 days.

(21) Appl. No.: 17/022,488

(22) Filed: Sep. 16, 2020

(65) Prior Publication Data

US 2021/0003655 A1 Jan. 7, 2021

Related U.S. Application Data (63) Continuation of application No. 15/664,342, filed on Jul. 31, 2017, now Pat. No. 10,852,383, which is a
(Continued)

(51) Int. Cl.
G01R 35/00 (2006.01)
G01C 17/38 (2006.01)
(Continued)

(52) U.S. Cl.
CPC ............ G01R 35/005 (2013.01); A61B 34/10 (2016.02); A61B 34/20 (2016.02); G01C 17/38 (2013.01);
(Continued)

(58) Field of Classification Search
CPC .................................................. G01R 35/005
(Continued)

(56) References Cited

U.S. PATENT DOCUMENTS 7,640,106 B1 * 12/2009 Stokar ..................... G06F 3/017
701/507
9,141,194 B1 9/2015 Keyes et al.
(Continued)

FOREIGN PATENT DOCUMENTS

AU 2016369607 12/2015
AU 2016369607 2/2019
(Continued)

OTHER PUBLICATIONS

Skog, Isaac, and Peter Händel. "Calibration of a MEMS inertial measurement unit." XVII IMEKO world congress. 2006. (Year: 2006).*
(Continued)

*Primary Examiner* — Walter L Lindsay, Jr.
*Assistant Examiner* — Philipmarcus T Fadul
(74) *Attorney, Agent, or Firm* — Allen, Dyer, Doppelt + Gilchrist, P.A.

(57) ABSTRACT

A method of calibrating an inertial measurement unit, the method comprising: (a) collecting data from the inertial measurement unit while stationary as a first step; (b) collecting data from the inertial measurement unit while repositioning the inertial measurement unit around three orthogonal axes of the inertial measurement unit as a second step; (c) calibrating a plurality of gyroscopes using the data collected during the first step and the second step; (d) calibrating a plurality of magnetometers using the data collected during the first step and the second step; (e) calibrating a plurality of accelerometers using the data collected during the first step and the second step; (f) where calibrating the plurality of magnetometers includes extracting parameters for distortion detection and using the extracted parameters to determine if magnetic distortion is present within a local field of the inertial measurement unit.

17 Claims, 3 Drawing Sheets

Related U.S. Application Data continuation of application No. 15/382,546, filed on Dec. 16, 2016, now abandoned.

(60) Provisional application No. 62/268,175, filed on Dec. 16, 2015.

(51) Int. Cl.

| | | |
|---|---|---|
| *A61B 34/10* | (2016.01) | |
| *A61B 34/20* | (2016.01) | |
| *G01C 21/16* | (2006.01) | |
| *G01C 25/00* | (2006.01) | |
| *G01P 21/00* | (2006.01) | |
| *A61B 17/00* | (2006.01) | |
| *A61B 5/06* | (2006.01) | |
| *A61B 5/00* | (2006.01) | |

(52) U.S. Cl.
CPC ........... *G01C 21/16* (2013.01); *G01C 25/005* (2013.01); *G01P 21/00* (2013.01); *A61B 5/065* (2013.01); *A61B 5/7242* (2013.01); *A61B 2017/00725* (2013.01); *A61B 2034/102* (2016.02); *A61B 2034/105* (2016.02); *A61B 2034/108* (2016.02); *A61B 2034/2048* (2016.02); *A61B 2560/0223* (2013.01); *A61B 2562/0219* (2013.01)

(58) Field of Classification Search
USPC .......................................................... 73/1.37
See application file for complete search history.

(56) References Cited

U.S. PATENT DOCUMENTS

| | | |
|---|---|---|
| 2006/0184336 A1 | 8/2006 | Kolen |
| 2007/0001920 A1 | 1/2007 | Webb et al. |
| 2007/0032748 A1 | 2/2007 | Mcneil et al. |
| 2007/0085528 A1 | 4/2007 | Govari et al. |
| 2010/0063763 A1 | 3/2010 | Rozelle |
| 2010/0310141 A1 | 12/2010 | Wilson |
| 2011/0063167 A1 | 3/2011 | Gum et al. |
| 2011/0106477 A1 | 5/2011 | Brunner |
| 2011/0199274 A1 | 8/2011 | Dalmazzo |
| 2011/0208473 A1 | 8/2011 | Bassompiere et al. |
| 2011/0248704 A1 | 10/2011 | Chowdhary et al. |
| 2011/0320153 A1 | 12/2011 | Lightcap et al. |
| 2012/0209117 A1 | 8/2012 | Mozes et al. |
| 2013/0046489 A1 | 2/2013 | Keal |
| 2013/0185018 A1* | 7/2013 | Sheng .................. G01C 21/165 702/153 |
| 2013/0217998 A1* | 8/2013 | Mahfouz .............. A61B 5/1036 600/595 |
| 2014/0275987 A1 | 9/2014 | Bzostek et al. |
| 2014/0278183 A1 | 9/2014 | Zheng et al. |
| 2015/0019159 A1 | 1/2015 | Elgersma et al. |
| 2017/0066464 A1* | 3/2017 | Carter ................... G05D 1/028 |
| 2018/0188284 A1 | 7/2018 | Douglas et al. |
| 2020/0233053 A1 | 7/2020 | Vissiere et al. |

FOREIGN PATENT DOCUMENTS

| | | |
|---|---|---|
| JP | H0996534 | 4/1997 |
| JP | 2007040762 | 2/2007 |
| JP | 2011220825 | 11/2011 |
| JP | 2013510318 | 3/2013 |
| JP | 2015203641 | 11/2015 |
| WO | 2015031072 | 3/2015 |
| WO | PCT/US2014/051173 | 3/2015 |
| WO | 2015089118 | 6/2015 |
| WO | PCT/US2014/069411 | 6/2015 |
| WO | PCT/US2014/051173 | 1/2016 |
| WO | PCT/US2014/069411 | 6/2016 |
| WO | 2017106794 | 6/2017 |
| WO | PCT/US2016/067387 | 6/2017 |
| WO | PCT/US2016/067387 | 6/2018 |

OTHER PUBLICATIONS

Fong et al., "Methods for In-Field User Calibration of an Inertial Measurement Unit Without External Equipment.," Measurement Science and Technology, vol. 19, No. 8, Jul. 10, 2008, pp.

\* cited by examiner

IMU CALIBRATION

CROSS REFERENCE TO RELATED APPLICATIONS

The present application is a continuation of U.S. patent application Ser. No. 15/664,342, filed Jul. 31, 2017 and titled "IMU Calibration," now U.S. Pat. No. 10,852,383, which is a continuation of U.S. Nonprovisional patent application Ser. No. 15/382,546, titled "IMU CALIBRATION," filed Dec. 16, 2016, now abandoned, and claims the benefit of U.S. Provisional Patent Application Ser. No. 62/268,175, titled "IMU CALIBRATION," filed Dec. 16, 2015, the disclosure of each of which is incorporated herein by reference.

INTRODUCTION TO THE INVENTION

The present disclosure is directed to methods and techniques for calibrating inertial measurement units (IMUs) and, more specifically, to methods and techniques that involve calibrating IMUs to account for local environments within which the IMUs operate.

It should be noted that Patent Cooperation Treaty application PCT/US14/69411, filed Dec. 9, 2014 is hereby incorporated by reference and appended hereto as Appendix A.

DETAILED DESCRIPTION

The exemplary embodiments of the present disclosure are described and illustrated below to encompass inertial measurement units and methods of calibrating the same. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Many current devices make use of integrated sensor components to capture and track information related to the use, location, and status of the device. One such system, the inertial measurement unit (IMU), is used to track object motion. A common packaging of an IMU comprises a single integrated circuit (IC) consisting of multiple inertial sensors, which can be a combination of accelerometers, gyroscopes, and magnetometers. These three sensor types can also be separated into individual ICs populated on the same circuit board. These two cases (single IC and multiple ICs) can be considered the same for purposes of the instant disclosure.

For all such sensors of the IMU, a calibration step may be performed to ensure the proper referencing and operation in the local environment. For example, accelerometers may be calibrated to determine a reference with respect to the direction of gravity and gyroscopes may be calibrated to some known rotational velocity. Magnetometer calibration is more complex, as the process requires knowledge of the local magnetic field strength and direction at a multitude of magnetometer orientations. The local environment calibration can be carried out by hand or by machine. The minimum considerations for local environment calibration should involve maneuvering of the IMU around the three orthogonal axes of the IMU, and a stationary period.

For applications requiring highly reliable and reproducible calibration of an IMU, a calibration machine may be used. A calibration machine may be constructed so that it does not introduce additional magnetic distortion to the IMUS. The calibration machine should produce movement for calibration for all the sensors of the IMU as well as movement in order for an algorithm to inspect the quality of the calibration.

The process for calibrating measurements from uncalibrated accelerometers, gyroscopes, and magnetometers of an IMU is described hereafter. This exemplary process is applicable to a single IMU or multiple IMUS populated on the same circuit board, where all sensors (uncalibrated accelerometers, gyroscopes, and magnetometers) may be calibrated simultaneously.

In exemplary form, the calibration procedure may include the following routines to allow adequate data to calculate and verify the calibration. This exemplary calibration comprises four stages that include, without limitation: (1) calibrating the gyroscopes; (2) calibrating the magnetometers routine; (3) calibrating the accelerometer routine; and, (4) calibrating the checking/validation routine.

Calibrating the gyroscopes of each IMU should provide for the gyroscopes being stationary for a set amount of time. As part of calibrating the gyroscopes, the instant process is determining the bias of the gyroscope by arithmetic mean as set forth in Equation 1 immediately below:

$$Gyro_{mean_i}[\ldots] = \overline{DATA_{gyro_i}}_{gyro\ calibration}, i = 1, 2, \ldots \quad \text{Equation 1}$$

Calibrating the magnetometers of each IMU should involve rotating the IMU around all of its orthogonal axes. In this fashion, this magnetometer calibration process first determines the soft and hard iron distortion using multi-dimensional Ellipsoidal Fitting function (EF_fun) set forth in Equation 2 immediately below:

$$SFe_{orig_i}, \quad \text{Equation 2}$$
$$HFe_{orig_i} = EF_{fun(DATA_{mag_i}[Mag\ calibration\ begin \to end])},$$
$$i = 1, 2, \ldots$$

where: $SFe_{orig}$ is the transformation of ellipsoid to sphere, and $HFe_{orig}$ is the sensor and local bias.

The resultant data from Equation 2 are then processed using Equation 3, shown immediately below:

$$procMAG_{orig_i} = \quad \text{Equation 3}$$
$$processMag(DATA_{mag_i}[Acc\ calibration\ \text{ration begin} \rightarrow$$
$$\text{end of checking routine}],$$
$$SFe_{orig_i}, HFe_{orig_i}), i = 1, 2, \ldots)$$

Thereafter, the alignment differences among magnetometers are calibrated. In doing so, Equation 4 may be utilized, with the assumption that all magnetometers are aligned to a reference alignment using this equation. Alternatively, the magnetometers may be aligned to a different reference alignment if desired. In Equation 4, $TMAG_{ij}$ represents the alignment transformation of magnetometer "j" to reference magnetometer "i".

$$TMAG_{ij} = procMAG_{orig_j} \setminus procMAG_{orig_i}, \quad \text{Equation 4}$$
$$i = 1, j = 2, 3 \ldots$$

Calibrating the accelerometers of each IMU should involve rotating the IMU around two axes perpendicular to gravity. In this fashion, the accelerometer calibration is calculated with the multi-dimensional Ellipsoidal Fitting function (EF_fun) set forth immediately below as Equation 5:

$$AccScale_{orig_i}, \quad \text{Equation 5}$$
$$AccBias_{orig_i} = EF_{fun}(DATA_{Acc_i}[Acc\ calibration\ \text{begin} \rightarrow end]),$$
$$i = 1, 2, \ldots$$

Calibrating the checking routine should involve rotating the IMU around the axis collinear with gravity. The result is best if the motion of the checking routine is performed multiple times at different angles with respect to gravity.

After calibrating the sensors, one may take into account manufacturing and IC assembly placement errors to extract or account for these errors. In this fashion, the instant disclosure includes a calibration sequence taking into account any mal-alignment among sensors, which are calibrated according to Equation 6-10 (applying the calibration parameters) provided immediately below. In doing so, all sensor data collected during the calibration may be subject to these calibration equations/parameters.

| | |
|---|---|
| $procGyro_i = processGyro(DATA_{gyro_i}, Gyro_{bias_i})$, $i = 1, 2, \ldots$ | Equation 6 |
| $procAcc_i = processAcc(DATA_{Acc_i}, Acc_{bias_i})$, $i = 1, 2, \ldots$ | Equation 7 |
| $procMAG_i = processMag(DATA_{mag_i}, SFe_{orig_i}, HFe_{orig_i})$, $i = 1, 2, \ldots$ | Equation 8 |
| Continuing the example as aligning all magnetometer to the first one, | |
| $alignProcMAG_j = procMAG_j * TMAG_{ij}$, $i = 1, j = 2, 3 \ldots$ | Equation 9 |
| $alignProcMAG_i = procMAG_i$ | Equation 10 |

With multiple IMUs rigidly fixed together, the aligned and calibrated signals should be roughly equal among each sensor type in the case of no noise or isotropic (to the sensor) noise.

Despite calibration with the local environment, magnetometers are especially prone to transient local disturbance. Specifically, introduction of additional ferromagnetic sources or movement of ferromagnetic sources after initial calibration (described previously) can distort the sensor signal and result in inaccurate readings. Distortion states can be classified as hard iron distortion, which is primary caused by the introduction of ferromagnetic materials such as steel tools that can deflect the field lines and produce an offset on the magnetometer sensors, and soft iron distortion, which is caused by an irregular magnetic field (such as magnets) that can alter the shape of the magnetic field. Given that these devices causing distortions will enter and exit the application field (area of use) of the IMU at unpredictable orientations, positions, and times, it is desirable that these distortions be detected and accounted for. By way of example, one area where distortions are commonplace is an operating room during a surgical procedure. More specifically, surgical instruments within an operating room are frequently repositioned within the operating field at different times and locations depending on the stage of the surgical procedure, which necessarily causes magnetic field distortions. It should be noted, however, that the exemplary disclosure is not limited to calibration of IMUs for surgical navigation or any particular field of use. Rather, the instant disclosure is applicable to calibrating any IMU in any field of use where local distortions may be present.

There are two essential parts to detect transient magnetic distortion. The first part is that the IMU must comprise two or more magnetometers (that may be populated on a common circuit board). The magnetometers are calibrated and aligned based the foregoing calibration teachings. The second part is the detection algorithm, which consists of two processes: (1) extracting parameters for distortion detection, which are calculated from the calibration data; and, (2) use of extracted parameters on captured IMU data to check if distortion is present.

What follows is a detailed explanation for calculating appropriate distortion threshold parameters. In general, one may use an algorithm for this calculation that may make use of the following assumptions: (1) IMU motion (or lack of motion) is detectable by all IMUs (accelerometer, gyroscope and magnetometer); (2) the angle and length of the calibrated magnetometers should have approximately identical values; (3) the calibrated magnetometer vectors should be approximately unity in magnitude; (4) the angle between the calibrated magnetometer vector and calibrated accelerometer vector should not change; (5) the radius of the calibrated magnetometers should be approximately equal to one; and, (6) the quaternions calculated using different magnetometers should be approximately equal.

Sufficient deviation from assumption 1 is deemed a motion anomaly and deviations from assumptions 2-6 are deemed a magnetic anomaly. Parameters for motion detection are calculated for each IMU sensor (accelerometer, gyroscope, and magnetometer) using data collected during local environment calibration. Using stationary and dynamic data, appropriate thresholds of motion are calculated for every IMU sensor, so that the calibrated IMU sensor output above the threshold indicates that the sensor is in motion and below which the sensor can be considered stationary (see Equation 2). A motion anomaly is considered to occur as in Table (2), which is described in more detail hereafter. In short, if a magnetometer has detected motion, but other sensors do not, a motion anomaly is said to exist.

For the magnetic anomaly, a deviation from assumption 2 is used to create a cost function, which is calculated as the magnitude of the vector difference weighted with the angular derivation between the vectors (see Algorithm 1 and Algorithm 4). During local environment calibration, expected values for the deviation from unity and from identical signals are calculated to form a cost function. The threshold is calculated from the value of this cost function during local environment calibration (when no additional distortion is presented). Then, as part of an anomaly detection process, any values of this cost function above the threshold are considered a magnetic anomaly.

For assumption 3, the magnetic strength is calculated as the mean of combined magnitudes (Algorithm (5)), which without noise is expected to be approximately 1. Then, as part of the anomaly detection process, any value outside the calculated magnetic strength (including a preset tolerance) is considered an anomaly.

For assumption 4, the derivation is calculated as the angular derivation between the magnetometer and the accelerometer vectors (Algorithm (6)). Then, as part of the anomaly detection process, any value outside the calculated angle (including a preset tolerance) is considered an anomaly.

For assumption 5, the deviation is calculated by using all of the magnetometer readouts, along with a preset of artificial points, to estimate a radius of the magnetic field using an ellipsoid estimation function as shown in Algorithm (7). The artificial points are used to support the estimation calculation. However, if the IMU contains more than 11 magnetometers, no artificial point is needed to resolve the radius. Then, as part of the anomaly detection process, any value outside the calculated radii (including a preset tolerance) is considered an anomaly.

For assumption 6, the deviation is determined by first calculating the orientation of the IMU using sensor fusion algorithm (e.g. Extended Kalman Filter) using different magnetometers as input, and an angular difference among the output orientation is calculated as shown in Algorithm (8). Then, as part of the anomaly detection process, any values greater than the angular different with a preset tolerance is considered an anomaly.

If motion or magnetic anomaly occurs, some unaccounted for magnetic distortion is present. An alert system for distortion provides feedback indicating the reliability of the orientation reported by the sensors may be inaccurate. What follows is a more detailed discussion of the algorithms utilized to detect motion and magnetic anomalies.

The anomaly detection is based on three categories of detection. The first is sensor fault detection, the second is magnetometer radii verification, and the third is quaternion output discrepancies. Sensor fault detection consists of the following functions: (i) motion and magnetic anomalies; (ii) magnetic strength; and (iii) angle between magnetometer and accelerometer vectors. The following method is used to consistently extract threshold values (TVs) for motion anomalies and cost functions from the calibration. The method utilizes Algorithm (1) as follows:

---

Algorithm (1)

Iteration: for [beginning of gyro calibration → end of checking routines]
$Gyro_{mean_i}[\ldots] = |\overline{procGyro_{current-kernel}^{current}}|, i = 1, 2, \ldots$
$Gyro_{std_i}[\ldots] = std(procGyro[current - kernel \to current]), i = 1, 2, \ldots$
$Acc_{std_i}[\ldots] = std(procAcc_i[current - kernel \to current]), i = 1, 2, \ldots$
$Mag_{std_i}[\ldots] = std(alignProcMAG_i[current - kernel \to current]), i = 1, 2, \ldots$ $$lenDiff_{i,j}[\ldots] = \frac{\sqrt{\sum_{axis}\left(\sum_{current-kernel}^{current}(alignProcMAG_i - alignProcMAG_j)^2\right)}}{kernel},$$
$i \neq j, i = 1, 2 \ldots, j = 1, 2 \ldots$ $$angDiff_{i,j}[\ldots] = \frac{\left|1 - \left(\overline{alignProcMAG_{i_{current-kernel}}^{current}} \cdot \overline{alignProcMAG_{j_{current-kernel}}^{current}}\right)\right|}{norm(\overline{alignProcMAG_{i_{current-kernel}}^{current}}) \cdot norm(\overline{alignProcMAG_{j_{current-kernel}}^{current}})},$$
$i \neq j, i = 1, 2 \ldots, j = 1, 2 \ldots$ $metricLenAng_{i,j}[\ldots] = lenDiff_{i,j}[\ldots] * angDiff_{i,j}[\ldots], i \neq j, i = 1, 2 \ldots, j = 1, 2 \ldots$ $$currentMagVal[\ldots] = \frac{1}{\max(i)\left(\sum \sqrt{\sum_{current-kernel}^{current}(alignProcMAG_i * alignProcMAG_j)}\right)},$$
$i \neq j, i = 1, 2 \ldots, j = 1, 2 \ldots$ End

---

Once the iteration from Algorithm (1) is completed, the mu and sigma of the cost function can be determined using Equations 11 and 12, immediately recited below.

---

$\mu = \overline{currentMagVal}_{mag\ and\ acc\ calibration}$  Equation 11
$\delta = SSF1 * std(currentMagVal)_{mag\ and\ acc\ calibration}$  Equation 12
Where: (a) SSF1 is a sensitivity scale factor; and,
(b) δ serves as the detection tolerance based on standard derivation (i.e., how many standard deviations away from the mean is considered acceptable).

---

Algorithm (2) is utilized to calculate motion and no motion (stationary) states for the sensors.

---

Algorithm (2)

$Stationary_{gyro_{std}} = \overline{Gyro}_{std_{gyro\ calibration}}$
$Motion_{gyro_{std}} = \overline{Gyro}_{std_{acc\ calibration}}$
$Stationary_{gyro_{mean}} = \overline{Gyro}_{mean_{gyro\ calibration}}$
$Motion_{gyro_{mean}} = \overline{Gyro}_{mean_{acc\ calibration}}$ -continued Algorithm (2)

$Stationary_{Acc_i} = \overline{Acc_{t_{std}}}_{gyro\ calibration}$, $i = 1, 2, \ldots$ $Motion_{Acc_i} = \overline{Acc_{t_{std}}}_{acc\ calibration}$, $i = 1, 2, \ldots$ $Stationary_{MAG_i} = \overline{MAG_{t_{std}}}_{gyro\ calibration}$, $i = 1, 2, \ldots$ $Motion_{MAG_i} = \overline{MAG_{t_{std}}}_{Checking\ routine}$, $i = 1, 2, \ldots$ A check is performed here to ensure all motion states should have values greater than the corresponding stationary states.

Algorithm (3) is utilized to calculate TVs for motion anomalies.

Algorithm (3)

$TV_{gyro_{std}} = SSF2 * (Motion_{gyro_{std}} - Stationary_{gyro_{std}}) + Stationary_{gyro_{std}}$
$TV_{gyro_{mean}} = SSF3 * (Motion_{gyro_{mean}} - Stationary_{gyro_{std}}) + Stationary_{gyro_{mean}}$
$TV_{Acc_i} = SSF4 * (Motion_{Acc_i} - Stationary_{Acc_i}) + Stationary_{Acc_i}$,
$i = 1, 2, \ldots$
$TV_{MAG_i} = SSF5 * (Motion_{MAG_i} - Stationary_{MAG_i}) + Stationary_{MAG_i}$,
$i = 1, 2, \ldots$ SSF2 to SSF5 are the sensitivity scale factor. It is typically set between 0 and 1, and should be adjusted based on sensors and desired sensitivity of the detection method.

Determination of a magnetic anomaly may be based upon a cost function TV, which is accomplished by calculating the cost function over the period of the calibration period as set forth in Algorithm (4).

Algorithm (4)

Iteration: for [beginning of gyro calibration → beginning of Check 1]

$pdfVal[\ldots] = \frac{1}{\sqrt{2\pi} * \delta} e^{-0.5*\left(\frac{(1-\mu)}{\delta}\right)^2} - \frac{1}{\sqrt{2\pi} * \delta} e^{-0.5*\left(\frac{(currentMagVal[\ldots]-\mu)}{\delta}\right)^2}$ $costFunction[\ldots] = SSF6 * \left| pdfVal[\ldots] * \frac{\sum metricLenAng_{i,j}[\ldots]}{\max(i)} \right|$, $i \neq j$, $i = 1, 2 \ldots$, $j = 1, 2 \ldots$ end
$TV_{costFunction} = \max(costFunction) + \overline{(costFunction)} + std(costFunction)$
SSF6 is a scale factor that is used to prevent losing the precision of the cost function from the small number.

In order to consistently extract TVs for discerning the strength of a magnetic anomaly from the calibration data, one can use Algorithm (5).

Algorithm (5)

Iteration: for [beginning of mag calibration → end of mag calibration]

$MagStr_i[\ldots] = \sqrt{\sum_{axis}(alignProcMAG_i)}$ $i = 1, 2, \ldots$

Algorithm (5)

end
$min\_MagStr_i = \min(MagStr_i)$ $i = 1, 2, \ldots$
$max\_MagStr_i = \max(MagStr_i)$ $i = 1, 2, \ldots$ In order to consistently extract TVs for discerning the angle between magnetometer and accelerometer vectors from the calibration data, one can use Algorithm (6).

Algorithm (6)

Iteration: for [beginning of gyro calibration → end of checking routine]
Use Extended Kalman Filter to estimation the orientation during the calibration
$q_i[\ldots] = EKF(procGyro, procAcc, alignProcMAG_i)$, $i = 1, 2, \ldots$
$e_i[\ldots] = [q2_i \quad q3_i \quad q4_i]$, $i = 1, 2, \ldots$ $\hat{e}_i[\ldots] = \begin{bmatrix} 0 & -q4_i & q3_i \\ q4_i & 0 & -q2_i \\ -q3_i & q2_i & 0 \end{bmatrix}$, $i = 1, 2, \ldots$ $Rp_i[\ldots] = (q1_i^2 - e_i'e_i) * I_{3\times 3} + 2(e_ie_i') - 2q1_i\hat{e}_i$, $i = 1, 2, \ldots$
$MF_i[\ldots] = Rp_i * alignProcMAG_i$, $i = 1, 2, \ldots$
$GF_i[\ldots] = Rp_i * procAcc$, $i = 1, 2, \ldots$ $\angle GM_i[\ldots] = acos\left[\frac{MF_i \cdot GF_i}{\|MF_i\| * \|GF_i\|}\right]$, $i = 1, 2, \ldots$ end
$min\angle TV\_GM_i = \overline{\angle GM_i} - tol1$
$max\angle TV\_GM_i = \overline{\angle GM_i} + tol2$
Where: to/1 and to/2 are tolerances for the detection threshold.

A magnetometer radii check calculation is performed on the calibrated magnetometer data before alignment. The radii of a normal point set should be equal to one. Algorithm (7) may be used to determine the radii threshold. As part of using Algorithm (7), a set of artificial points on a unit sphere are created or generated, where the set of points should be close to evenly distributed and have a minimum of 18 points. Using an ellipsoid fitting method on the artificial points, one can utilize the processed magnetometer data to determine the radii as set forth below Algorithm (7)

Radii = ellipsoidFit([artificial points, procMAG_i], $i = 1, 2 \ldots$
minRadii = $\overline{Radii}$ - tol3

-continued

Algorithm (7)

maxRadii = $\overline{Radii}$ + tol4
Where: tol3 and tol4 are tolerances for the detection threshold; and, minRadii and maxRadii should be within 0.93 and 1.07 for applications that require high reliability.

Quaternion output discrepancies is a detection method that is based on the orientation output calculated from using different magnetometers. The following algorithm, Algorithm (8), may be used to determine the quaternion output discrepancies threshold, using the quaternions output from Algorithm (6), and calculate the angle between the quaternions.

Algorithm (8)

qDiff$_{i,j}$[ . . . ] = quatAngleDiff(q$_i$[ . . . ], q$_j$[ . . . ]), i ≠ j, i = 1, 2 . . . , j = 1, 2 . . .
TV_qDiff$_{i,j}$ = $\overline{qDiff_{i,j}[...]}$ + SSF7 * std(qDiff$_{i,j}$[ . . . ]), i ≠ j, i = 1, 2 . . . , j = 1, 2 . . .

After extracting the TVs for anomaly detection, the following calculation may be used to determine if the IMU is being affected by a local anomaly. As a prefatory step, all incoming sensor data may be processed using Equations 1-10 discussed previously. In addition, Algorithms (1) and (4) may be utilized to determine relative deviation among magnetometers within a preset kernel size. For the exemplary sensor fault detection system, the motion is detected based on the following rules in Table (1).

TABLE (1)

Motion Detection based on sensors

| Activity | Condition | Result |
|---|---|---|
| Gyro has detected motion | If std(procGyro$_i$) > TV$_{gyro_{std_i}}$, i = 1, 2, . . . OR $|\overline{procGyro_i}|$ > TV$_{gyro_{mean_i}}$, i = 1, 2, . . . | inertial_motion_detection = 1 |
| Accelerometer has detected motion | If std(procAcc$_i$) > TV$_{Acc_i}$, = 1, 2, . . . | inertial_motion_detection = 1 |
| Magnetometer has detected motion | If std(procMAG$_i$) > TV$_{MAG_i}$, i = 1, 2, . . . | Magnetic_motion_detection = 1 |

Within the preset kernel size, the following rules in Table (2) are used to detect a motion anomaly.

TABLE (2)

Motion anomaly detection

| Motion Anomaly Flag | Condition |
|---|---|
| False | If Σinertial_motion_detection > 1 AND Σmagnetic_motion_detection > 1 |
| False | If Σinertial_motion_detection < 1 AND Σmagnetic_motion_detection < 1 |
| True | If Σinertial_motion_detection < 1 AND Σmagnetic_motion_detection > 1 |
| False | If Σinertial_motion_detection > 1 AND Σmagnetic_motion_detection < 1 |

The following rules in Table (3) are used to detect a magnetic anomaly.

TABLE (3)

Magnetic Anomaly detection

| Magnetic Anomaly Flag | Condition |
|---|---|
| True | costFunction > TV$_{costFunction}$ |
| False | costFunction ≤ TV$_{costFunction}$ |

In accordance with the instant disclosure, one can calculate the magnetic strength using Algorithm (5). Thereafter, using the rules of Table (4), one can discern whether a magnetic anomaly is present.

TABLE (4)

Magnetic strength anomaly detection

| Magnetic Strength Anomaly Flag | Condition |
|---|---|
| True | MagStr$_i$ < min_MagStr$_i$ OR MagStr$_i$ > max_MagStr$_i$ |
| False | MagStr$_i$ ≥ min_MagStr$_i$ OR MagStr$_i$ ≤ max_MagStr$_i$ |

In accordance with the instant disclosure, one can determine the angle between magnetometer and accelerometer vectors using Algorithm (6). This detection is only activated when the IMU/sensors is/are stationary, which is detected from the motion detection algorithm. Using the following table, Table (5), one can discern whether a magnetometer and accelerometer vector anomaly is present.

TABLE (5)

magnetometer and accelerometer vectors anomaly detection

| MAG and ACC vectors Anomaly Flag | Condition |
|---|---|
| True | ∠LGM$_i$ < min∠TV_GM$_i$ OR ∠GM$_i$ > max∠TV_GM$_i$ |
| False | ∠LGM$_i$ ≥ min∠TV_GM$_i$ OR ∠GM$_i$ ≤ max∠TV_GM$_i$ |

In accordance with the instant disclosure, one can determine the magnetic radii by processing the raw data from the magnetometers using Algorithm (7). Using the following table, Table (6), one can discern whether a magnetic radii anomaly is present.

TABLE (6)

Magnetic Radii anomaly detection

| Magnetic Radii Anomaly Flag | Condition |
|---|---|
| True | radii < minRadii OR radii > maxRadii |
| False | radii ≥ minRadii OR radii ≤ maxRadii |

In accordance with the instant disclosure, one can calculate the orientation of the IMUs with Algorithm (6) and calculate the angular difference with Algorithm (8). Using the following table, Table (7), one can discern whether a quaternion output discrepancy is present.

TABLE (7)

Quaternion discrepancies detection

| Quaternion Discrepancies Flag | Condition |
|---|---|
| True | $qDiff_{i,j} > TV\_qDiff_{i,j}$ |
| False | $qDiff_{i,j} \leq TV\_qDiff_{i,j}$ |

Anomaly detection can be weighted using the output from each of these sub-detection systems, and determine the relevant level of disturbance detected by the system. For systems requiring high levels of reliability, it should be considered an anomaly if any of these subsystem flags is detected.

The following discussion describes a process for calibrating an IMU when it is being used with or in proximity to a ferromagnetic object. One example, in the medical device field of use, is during surgical navigation, where the IMU is needed to track the motion of a ferromagnetic object (e.g., tools made from stainless steel, CoCr, etc). Since local environment calibration is performed presumably without these ferromagnetic objects in proximity, there is no way to compensate for their distortions during the local environment calibration stage. A secondary calibration step should be undertaken to correct the distortion when ferromagnetic objects will be used in proximity to the IMUs. The proposed method accounts for the fact that an IMU may be rigidly fixed to the ferromagnetic object when in use.

While it is possible to manually maneuver the IMU attached to the ferromagnetic object to collect a lump sum of data for re-calibration, this method is inefficient and requires a substantial amount of time for the user to repeat the maneuver for each ferromagnetic object needing calibration. Secondly, it is possible that the calibration of the combined effect of the local environment and the ferromagnetic object is not aligned with the calibration of the local environment alone. Though either of the calibrations may be functional for yaw tracking, the latent transformation between calibrations on the reference field can produce errors. By way of example, one may think of it as comparing the reading of two compasses, one being horizontal to the ground, the other being tilted 5 degrees. The horizontal compass is calibrated to the local environment, while the other compass is calibrated with both ferromagnetic objects and local environment. While both calibrations are both functional, the reading from each compass will be different. Accordingly, an exemplary algorithm of the instant disclosure addresses both of these issues.

The instant approach makes use of the distortion characteristic of low field strength ferromagnetic objects, and models the correction based on a limited amount of data input. This enables a much simpler calibration maneuver, while still being able to achieve reasonable calibration.

Figure 1:
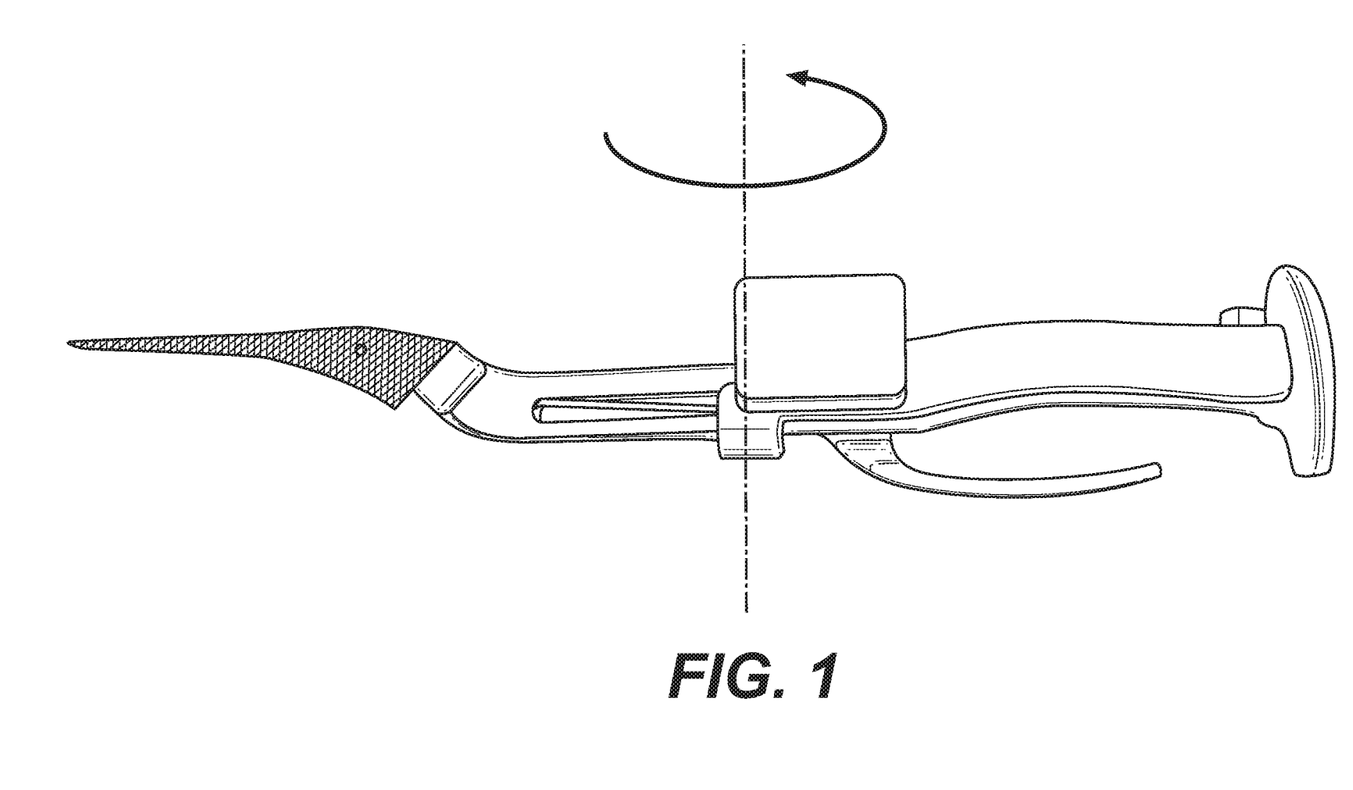
FIG. 1 is a graphical depiction of a ferromagnetic device mounted to an inertial measurement unit and being rotated around an X-axis.
Figure 2:
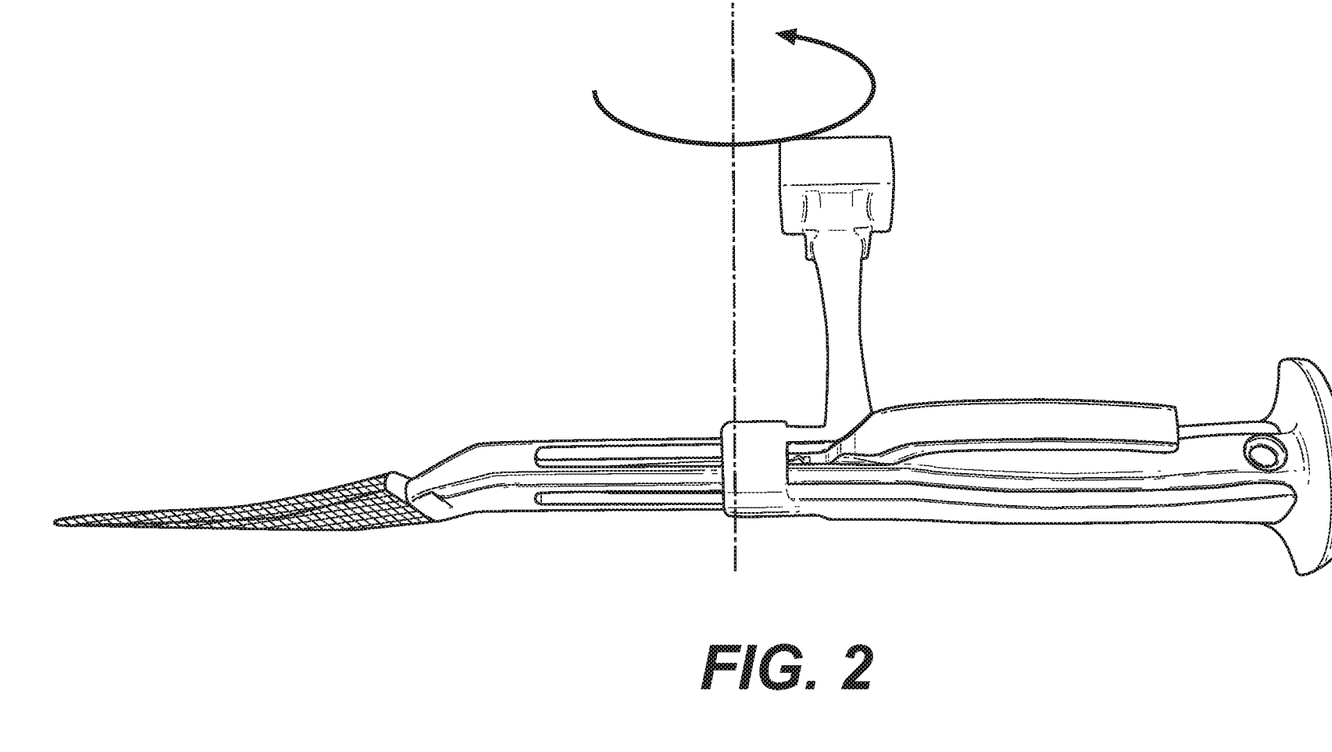
FIG. 2 is a graphical depiction of the ferromagnetic device mounted to the inertial measurement unit of FIG. 1, being rotated around a Y-axis.
Figure 3:
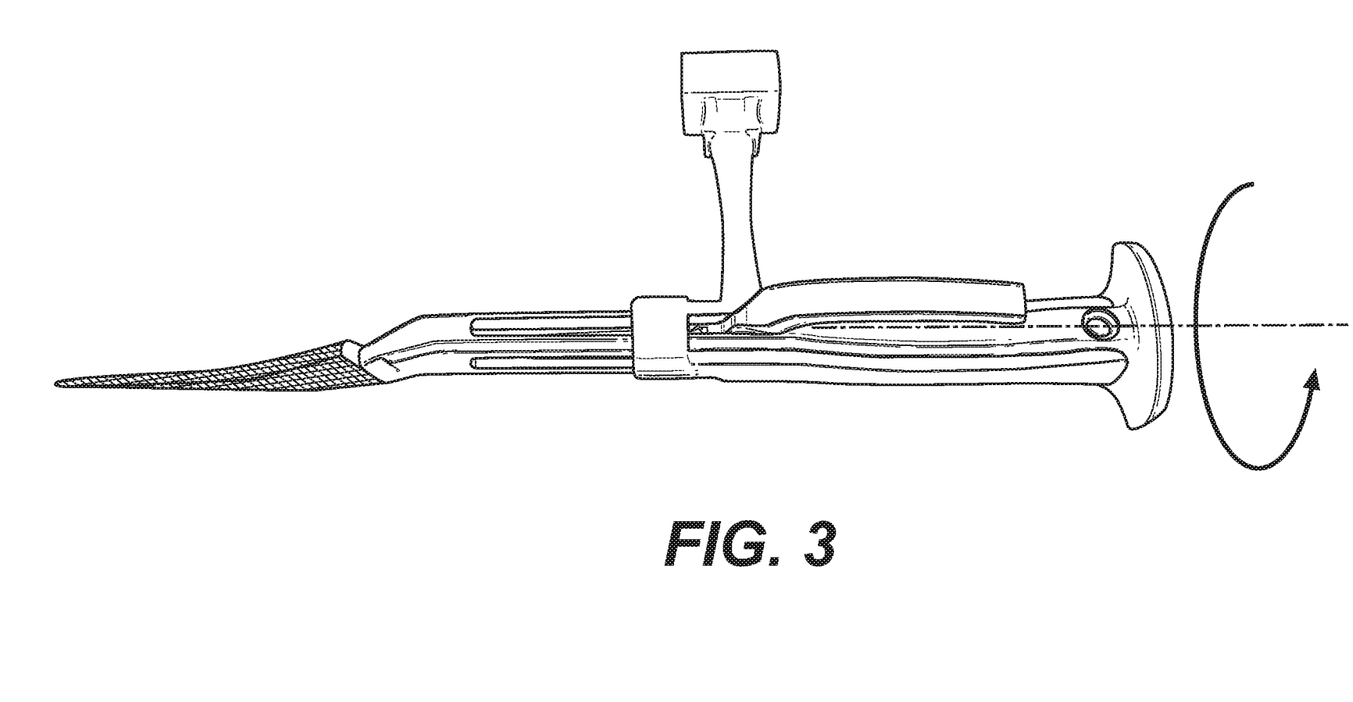
FIG. 3 is a graphical depiction of the ferromagnetic device mounted to the inertial measurement unit of FIG. 1, being rotated around a Z-axis.

Referring to FIGS. 1-3, the object 100 attached to the IMU 102 (or the IMU 102 by itself) is moved through a series of orientations—which can be confirmed from the IMU data. From the collected data, an initial estimation of the distortion field can be calculated through standard ellipsoid processing and analysis. A reference dataset (currently using 25000 vectors) is drawn from a von-Mises Fisher density, thereby creating a set of uniformly distributed vectors around the IMU sphere. The magnetic distortion calculated during the local environment calibration, and the initial estimation of magnetic distortion with the ferromagnetic object are applied in reverse to the reference dataset. This creates two datasets: (1) a reference dataset being distorted by the local environment; and, (2) a reference dataset being distorted by both the local environment and the attached ferromagnetic object 100 (or ferromagnetic object in proximity to the IMU 102). Since all the points between these two datasets originate from the same reference dataset, a point-to-point correspondence between local environment distortion, and local environment distortion with the ferromagnetic object is established. The correction for the ferromagnetic object is then extracted from the latter using a recursive optimization algorithm with the prior dataset.

This exemplary calibration process can be used for any number of objects, so that multiple objects which have latent magnetic fields can be used with the magnetometer without compromising sensor accuracy, as well as maintain a consistent reference field.

The following section outlines the algorithm for calibrating a ferromagnetic object with a pre-calibrated IMU. This part assumes that the IMU has been calibrated according to the foregoing discussion. The IMU, as part of this calibration sequence, should be rigidly attached to the tool or otherwise have the tool in a constant position with respect to the IMU. The operator rotates the object for at least one revolution along each axis in a standard Cartesian system as depicted in FIGS. 1-3. Once the tool calibration dataset is collected, the following algorithm can calculate and compensate the distortion.

As an initial matter, an initial guess is made as to the center offset of the data set using Equation 13 below.

$$SFe_{inst_i}, HFe_{inst_i} = EF_{fun}(DATA_{mag_i}), i = 1, 2, \ldots \qquad \text{Equation 13}$$

Thereafter, a large number (e.g., 25,000) of random 3D unit vectors are generated and application of the inverse of the original and instrument SFe on to them using Algorithm (9) below.

Algorithm (9)

Iteration: for 1 ... 25000
samples = rand3Dvectors
$samples_{distorted_i}$ = samples * $inv(SFe_{inst_i})$, i = 1, 2, ...
$samples_{normal_i}$ = samples * $inv(SFe_{orig_i})$, i = 1, 2, ...
End Using Equation 14, shown below, calculate the point correspondence transformation.

$$T_{iD \rightarrow N} = samples_{normal_i} \backslash samples_{distorted_i}, i=1,2, \qquad \text{Equation 14}$$

Using Equation 15, shown below, calculate the point-to-point distortion distance.

$$\text{Diff}_{ND_i} = \text{samples}_{normal_i} - \text{samples}_{distorted_i}, i=1,2, \quad \text{Equation 15}$$

Using Equation 16, shown below, for each axis, locate the maximum negative of $\text{Diff}_{ND}$.

$$loc_i = \text{minmax}(\text{Diff}_{ND_i}), i=1,2, \quad \text{Equation 16}$$

Using Equation 17, shown below, calculate the index location of loc.
The index location of loc is $$ind_i = \text{index}(\text{minmax}(\text{Diff}_{ND_i})), i=1,2, \quad \text{Equation 17}$$

Using Equation 18, shown below, calculate the center along the maximum distortion distance axes.

$$c_i = \min(loc_i) + \max(loc_i), i=1,2, \quad \text{Equation 18}$$

Using Equation 19, shown below, calculate the maximum correction boundaries.

$$\text{Dbound}_i = \text{samples}_{distorted_i}(ind_i), i=1,2, \quad \text{Equation 19}$$

Using Equation 20, shown below, after the distortion compensation parameters are calculated, center the instrument calibration dataset.

$$\text{centerMAG}_i = \text{DATA}_{mag_i} - \text{HFe}_{inst_i}, i=1,2, \quad \text{Equation 20}$$

The foregoing calibration correction can be applied in at least two ways. In a first fashion, the calibration correction is applied using a point correspondence transformation, such as Equation 21 shown below.

$$\text{compensatedMAG}_i = \text{centerMAG}_i * \text{inv}(T_{i_D \to N}) i=1,2, \quad \text{Equation 21}$$

Alternatively, in a second fashion, the calibration correction is applied using geometric scaling and compensation, such as by using Equations 22 and 23.

$$SF_i(X,Y,Z) = \frac{\text{centerMAG}_i(X,Y,Z) - c(X,Y,Z) \cdot \text{Dbound}_i(X,Y,Z) - c(X,Y,Z)}{\text{norm}(\text{centerMAG}_i(X,Y,Z) - c(X,Y,Z))}, \quad \text{Equation 22}$$
$$\text{norm}(\text{Dbound}_i(X,Y,Z) - c(X,Y,Z))$$
$$i=1,2,\ldots$$

$$\text{ccompensatedMAG}_i = \text{centerMAG}_i + loc_i * SF_i, i=1,2,\ldots \quad \text{Equation 23}$$

Using equation 24, the adjusted calibration parameters may be calculated.

$$SFe_{adjInst_i}, HFe_{adjInst_i} = \text{magCal}(\text{compensated MAG}_i), i=1,2, \quad \text{Equation 24}$$

Post conclusion of the foregoing calibration computations, the calibration computations may be applied to the magnetometers of each IMU that is attached to the ferromagnetic object or will be in a fixed positional relationship thereto. In order to apply the calibration computations to the magnetometers of each IMU, the magnetometer data is centered using Equation 20. By way of example, on may apply the correction to account for the distortion cause by the tool via a point correspondence transformation using Equation 21, or apply the geometric scaling and compensation using Equations 22 and 23. Thereafter, the magnetometers of the IMU can be processed by applying the adjusted soft and hard iron compensation parameters via Equation 25, shown below.

$$\text{procMAG}_i = \text{processMag}(\text{compensatedMAG}_i, SFe_{adjInst_i}, HFe_{adjInst_i}), i=1,2, \quad \text{Equation 25}$$

Once the magnetometers have been processed, the magnetometers are aligned using Equations 9 and 10

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of calibrating an inertial measurement unit, the inertial measurement unit comprising at least two magnetometers, and at least two accelerometers, the method comprising:
presuming at least one of the following: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal;
collecting data from the inertial measurement unit, while stationary as a first step;
collecting data from the inertial measurement unit while repositioning the inertial measurement unit as a second step;
calibrating the at least two magnetometers using the data collected during the first step and the second step; and
calibrating of the at least two accelerometers using the data collected during the first step and the second step.

2. The method of claim 1, wherein at least two of the following are presumed: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal.

3. The method of claim 1, wherein at least three of the following are presumed: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal.

4. The method of claim 1, wherein at least four of the following are presumed: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal.

5. The method of claim 1, wherein all five of the following are presumed: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal.

6. The method of any one of claims 1-5, wherein presuming the vector angle and the vector length of the at least two magnetometers have identical values, the method further comprising:
calculating a magnitude of vector angle differences weighted using angular derivation between the vector angles to form a cost function;
calculating a threshold using the cost function; and
establishing a presence of a magnetic anomaly based upon the threshold.

7. The method of any one of claims 1-5, wherein presuming each of the plurality of magnetometer vectors is one in magnitude, the method further comprising:
calculating magnetic strength as a mean of combined magnetic strengths from the at least two magnetometers;
establishing a tolerance for the calculated magnetic strength to create a magnetic strength range; and
establishing a presence of a magnetic anomaly based upon the magnetic strength range.

8. The method of any one of claims 1-5, wherein presuming the angle between the calibrated magnetometer vector and the calibrated accelerometer vector should not change, the method further comprising:
calculating angular derivation between a magnetometer vector and a accelerometer vector;
establishing a tolerance for the calculated angular derivation to create an angular derivation range; and
establishing a presence of a magnetic anomaly based upon the angular derivation range.

9. The method of any one of claims 1-5, wherein presuming the radius of the at least two magnetometers, post calibration, is equal to one, the method further comprising:
estimating a radius of a magnetic field using an ellipsoid estimation function and data from the at least two magnetometers;
establishing a tolerance for the estimated radius of the magnetic field to create a magnetic field radii range; and
establishing a presence of a magnetic anomaly based upon the magnetic field radii range.

10. The method of any one of claims 1-5, wherein presuming quaternions calculated using different ones of the at least two magnetometers are equal, the method further comprising:
calculating an orientation of the inertial measurement unit in quaternion for each of the at least two magnetometers using outputs from the at least two magnetometers;
determining a quaternion output discrepancies threshold using the calculated orientations of the inertial measurement unit in quaternion;
calculating an angle between the calculated orientations of the inertial measurement unit in quaternion;
establishing a tolerance for the calculated angle to create a quaternion angle range; and
establishing a presence of a magnetic anomaly based upon the quaternion angle range.

11. A method of calibrating at least two magnetometers of an inertial measurement unit, while the inertial measurement unit is near an operating room of a medical facility comprising a local environment, the inertial measurement unit including at least two accelerometers, the method comprising:
collecting data from the at least two magnetometers of the inertial measurement unit while the inertial measurement unit is rigidly attached to a ferromagnetic object and the ferromagnetic object is repositioned in the local environment;
calculating magnetic distortion from the data collected from the at least two magnetometers during repositioning the ferromagnetic object in the local environment;
applying the magnetic distortion to a reference dataset, the reference dataset comprising uniformly distributed vectors around a sphere, to create a first distorted dataset;
applying an initial magnetic distortion to the reference dataset, the initial magnetic distortion being from a prior calibration of the at least two magnetometers when not rigidly attached to the ferromagnetic object, to create a second distorted dataset; and
calibrating the at least two magnetometers to account for ferromagnetic distortion using a recursive optimization algorithm applied to both the first and second distorted datasets to extract the ferromagnetic distortion.

12. The method of claim 11, wherein the reference dataset comprises thousands of random three dimensional unit vectors drawn from a vin-Mises Fisher distribution around a sphere; and wherein application of the initial magnetic distortion and the magnetic distortion are applied in reverse to the reference dataset.

13. The method of claim 11, wherein the prior calibration of the at least two magnetometers includes:
presuming at least one of the following: (1) a vector angle and a vector length of each of the at least two magnetometers have identical values; (2) each of a plurality of magnetometer vectors is one in magnitude; (3) an angle between a calibrated magnetometer vector and a calibrated accelerometer vector should not change; (4) a radius of the at least two magnetometers, post calibration, is equal to one; and (5) quaternions calculated using different ones of the at least two magnetometers are equal;
collecting data from the inertial measurement unit, while stationary as a first step;
collecting data from the inertial measurement unit while repositioning the inertial measurement unit as a second step;
calibrating the at least two magnetometers using the data collected during the first step and the second step; and
calibrating of the at least two accelerometers using the data collected during the first step and the second step.

14. The method of claim 11, wherein collecting data from the at least two magnetometers of the inertial measurement unit while the inertial measurement unit is rigidly attached to the ferromagnetic object and repositioned includes repositioning the ferromagnetic object for at least one revolution around each Cartesian axis.

15. The method of claim 11, wherein calibrating the at least two magnetometers to account for ferromagnetic distortion includes centering the data collected from the at least two magnetometers.

16. The method of claim 15, wherein calibrating the at least two magnetometers to account for ferromagnetic distortion includes at least one of using a point correspondence transformation equation and using a geometric scaling and compensation equation.

17. The method of claim 11, wherein calibrating the at least two magnetometers to account for ferromagnetic distortion includes applying adjusted hard and soft iron compensation parameters.

\* \* \* \* \*